United States Patent [19]

Riechers et al.

[11] Patent Number: 6,111,100

[45] Date of Patent: Aug. 29, 2000

[54] PREPARATION OF BIS(2-MORPHOLINOETHYL) ETHER

[75] Inventors: Hartmut Riechers, Neustadt; Joachim Simon, Mannheim; Andreas Henne, Neustadt; Arthur Höhn, Kirchheim, all of Germany

[73] Assignee: BASF Aktiengesellschaft, Ludwigshafen, Germany

[21] Appl. No.: 09/474,906

[22] Filed: Dec. 30, 1999

[30] Foreign Application Priority Data

Jan. 14, 1999 [DE] Germany .................. 199 01 198

[51] Int. Cl.$^7$ .................................................. C07D 413/12
[52] U.S. Cl. .................................................. 544/87
[58] Field of Search .................................. 544/87

[56] References Cited

U.S. PATENT DOCUMENTS

| | | | |
|---|---|---|---|
| 3,645,925 | 2/1972 | Speranza et al. | 544/88 |
| 3,817,997 | 6/1974 | Carlson et al. | 544/83 |
| 4,647,663 | 3/1987 | Dixon et al. | 544/106 |

FOREIGN PATENT DOCUMENTS

| | | |
|---|---|---|
| 36 331 | 9/1981 | European Pat. Off. . |
| 716 084 | 6/1996 | European Pat. Off. . |

OTHER PUBLICATIONS

Selectivity Control in the Amination . . . Marsella, pp. 434–442, 1992.
The Soviet Chem. Ind., 14:11 (1982) Kronich et al. 1318–1324.

*Primary Examiner*—John M. Ford
*Attorney, Agent, or Firm*—Keil & Weinkauf

[57] ABSTRACT

In a process for preparing bis(2-morpholinoethyl) ether by reacting diethylene glycol with ammonia under superatmospheric pressure and at elevated temperature in the presence of hydrogen and a hydrogenation catalyst, the catalytically active composition of the catalyst prior to reduction with hydrogen comprises from 20 to 85% by weight of aluminum oxide ($Al_2O_3$), zirconium dioxide ($ZrO_2$), titanium dioxide ($TiO_2$) and/or silicon dioxide ($SiO_2$), from 1 to 70% by weight of oxygen-containing compounds of copper, calculated as CuO, from 0 to 50% by weight of oxygen-containing compounds of magnesium, calculated as MgO, oxygen-containing compounds of chromium, calculated as $Cr_2O_3$, oxygen-containing compounds of zinc, calculated as ZnO, oxygen-containing compounds of barium, calculated as BaO, and/or oxygen-containing compounds of calcium, calculated as CaO, and less than 20% by weight of oxygen-containing compounds of nickel, calculated as NiO, based on the oxygen-containing compounds of copper, calculated as CuO.

8 Claims, No Drawings

PREPARATION OF BIS(2-MORPHOLINOETHYL) ETHER

The present invention relates to a process for preparing bis(2-morpholinoethyl) ether (2,2'-dimorpholino(diethyl ether), DMDEE) of the formula I

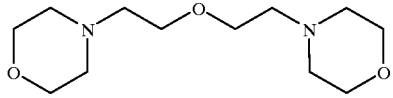

by reacting diethylene glycol (DEG) of the formula (II)

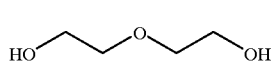

with ammonia under superatmospheric pressure and at elevated temperature in the presence of hydrogen and a hydrogenation catalyst.

bis(2-morpholinoethyl) ether (I) is a known polymerization catalyst in the preparation of polyurethanes (cf., for example: U.S. Pat. No. 3,645,925)

HU-A-212713 (Derwent Abstract No. 97-539345/50) describes the preparation of bis (2-morpholinoethyl) ether by catalytic reductive amination of diethylene glycol with morpholine in the presence of a copper-, chromium- and barium-containing catalyst.

EP-A-716 084 relates to a process for preparing bis (2-morpholinoethyl) ether and N-(2-(2-hydroxyethoxy) ethyl)morpholine by reacting diethylene glycol with morpholine in the presence of $H_2$ and a copper catalyst and in the absence of ammonia (cf. loc. cit.: page 3, lines 53 to 54).

JP-A-02 111 765 (Derwent Abstract No. 90-169102/22) describes the preparation of bis(2-morpholinoethyl) ethers in yields of from 67 to 94% by reacting substituted or unsubstituted morpholines with diethylene glycol in the presence of a Raney cobalt catalyst.

EP-A-36 331 and U.S. Pat. No. 4,647,663 describe a process for preparing morpholine and morpholine derivatives, with simultaneous formation of a small amount of bis(2-morpholinoethyl) ether as undesired by-product (cf. EP-A-36 331, page 4, lines 19 to 23), by reacting a dialkylene glycol with ammonia in the presence of $H_2$ and a hydrogenation catalyst in a trickle-bed reactor.

U.S. Pat. No. 3,817,997 describes a process for preparing bis(2-morpholinoethyl) ether by treatment of an amine residue, which is obtained in a catalytic reaction of diethylene glycol with ammonia, with a hydrogenation catalyst at elevated temperature and superatmospheric pressure.

Chem. Prum. (1992), 42(5–6), 105–9 (Chem. Abstr. 119: 72556) describes a gas-chromatographic analysis of by-products in crude products from the synthesis if morpholine from diethylene glycol and $NH_3$. According to this analysis, bis(2-morpholinoethyl) ether is formed as a by-product in relatively large amounts if the morpholine synthesis is carried out in the gas phase rather than in the liquid phase.

Adv. Chem. Ser. 1992, 230 (Homogeneous Transition Met. Catal. React.), 433–42 reports the formation of bis(2-morpholinoethyl) ether in a selectivity and yield of only 17% in the reaction of diethylene glycol with morpholine in the presence of a $RuCl_3 \cdot xH_2O$ *$3PBu_3$-catalyst (loc. cit.: Table V on page 440). A disadvantage here is the use of an expensive noble metal catalyst which, in addition, can be recycled only with difficulty.

Khim. Prom-st. (Moscow) (11), 653–5 (1982) (Chem. Abstr. 98: 91383q) describes the preparation of morpholine by gas-phase cycloamination of diethylene glycol with ammonia in the presence of $H_2$ and an Ni—Cu—$Cr_2O_3$ catalyst.

Zh. Vses. Khim. Obshchest. 14(5), 589–90 (1969) (Chem. Abstr. 72: 66879m) describes the formation of morpholine in a yield of 70% by gas-phase reaction of diethylene glycol with $NH_3$ over a nickel catalyst in the presence of $H_2$. Among other by-products, bis(2-morpholinoethyl) ether was isolated in a yield of from 5 to 7%.

The above-described processes give bis(2-morpholinoethyl) ether either only in very small yield or they start from expensive starting materials.

It is an object of the present invention to find an alternative, economical process for preparing bis(2-morpholinoethyl) ether.

We have found that this object is achieved by a process for preparing bis(2-morpholinoethyl) ether by reacting diethylene glycol with ammonia under superatmospheric pressure and at elevated temperature in the presence of hydrogen and a hydrogenation catalyst, wherein the catalytically active composition of the catalyst prior to reduction with hydrogen comprises from 20 to 85% by weight of aluminum oxide ($Al_2O_3$), zirconium dioxide ($ZrO_2$), titanium dioxide ($TiO_2$) and/or silicon dioxide ($SiO_2$), from 1 to 70% by weight of oxygen-containing compounds of copper, calculated as CuO, from 0 to 50% by weight of oxygen-containing compounds of magnesium, calculated as MgO, oxygen-containing compounds of chromium, calculated as $Cr_2O_3$, oxygen-containing compounds of zinc, calculated as ZnO, oxygen-containing compounds of barium, calculated as BaO, and/or oxygen-containing compounds of calcium, calculated as CaO, and less than 20% by weight of oxygen-containing compounds of nickel, calculated as NiO, based on the oxygen-containing compounds of copper, calculated as CuO.

In the process of the present invention, the catalysts used preferably consist only of catalytically active composition and, if desired, a shaping aid (e.g. graphite or stearic acid) if the catalyst is used as a shaped body, i.e. they contain no further catalytically active components.

In this context, the oxidic support materials titanium dioxide ($TiO_2$), aluminum oxide ($Al_2O_3$), zirconium dioxide ($ZrO_2$) and silicon dioxide ($SiO_2$) are counted as part of the catalytically active composition.

The catalysts are used by introducing the catalytically active composition milled to a powder into the reaction vessel or by locating the catalytically active composition as shaped bodies after milling, mixing with shaping aids, shaping and heat treatment, for example as pellets, spheres, rings or extrudates, in the reactor.

The concentrations given (in % by weight) for the components of the catalyst are in each case based, unless otherwise indicated, on the catalytically active composition of the finished catalyst after its last heat treatment and before it has been reduced with hydrogen.

The catalytically active composition of the catalyst after its last heat treatment and before it has been reduced with hydrogen is defined as the sum of the masses of the catalytically active constituents and the abovementioned catalyst support materials and comprises essentially the following constituents:

titanium dioxide (TiO$_2$) and/or aluminum oxide (Al$_2$O$_3$) and/or zirconium dioxide (ZrO$_2$) and/or silicon dioxide (SiO$_2$)

and oxygen-containing compounds of copper and, if desired, oxygen-containing compounds of magnesium and/or of chromium and/or of zinc and/or of barium and/or of calcium and, if desired, oxygen-containing compounds of nickel, where the amount of these oxygen-containing compounds of nickel, calculated as NiO and based on the amount of oxygen-containing compounds of copper, calculated as CuO, is less than 20% by weight.

The sum of the abovementioned constituents of the catalytically active composition, calculated as Al$_2$O$_3$, ZrO$_2$, TiO$_2$, SiO$_2$, CuO, MgO, Cr$_2$O$_3$, ZnO, BaO, CaO and NiO, is usually from 70 to 100% by weight, preferably from 80 to 100% by weight, particularly preferably from 90 to 100% by weight, very particularly preferably 100% by weight.

The catalytically active composition of the catalysts used in the process of the present invention may further comprise one or more elements (oxidation state 0) or their inorganic or organic compounds selected from groups I A to VI A and I B to VII B and VIII of the Periodic Table.

Examples of such elements and their compounds are:

Transition metals such as Co and CoO, Re and rhenium oxides, Mn and MnO$_2$, Mo and molybdenum oxides, W and tungsten oxides, Ta and tantalum oxides, Nb and niobium oxides or niobium oxalate, V and vanadium oxides and vanadiyl pyrophosphate; lanthanides such as Ce and CeO$_2$ or Pr and Pr$_2$O$_3$; alkali metal oxides such as Na$_2$O; alkali metal carbonates; alkaline earth metal oxides such as SrO; alkaline earth metal carbonates such as MgCO$_3$, CaCO$_3$ and BaCO$_3$; boron oxide (B$_2$O$_3$).

The catalytically active composition of the catalysts used in the process of the present invention comprises, after the catalysts have been subjected to their last heat treatment and before they have been reduced with hydrogen, from 20 to 85% by weight, preferably from 25 to 80% by weight, particularly preferably from 30 to 75% by weight, of aluminum oxide (Al$_2$O$_3$) and/or zirconium dioxide (ZrO$_2$) and/or titanium dioxide (TiO$_2$) and/or silicon dioxide (SiO$_2$) and from 1 to 70% by weight, preferably from 2 to 65% by weight, particularly preferably from 5 to 60% by weight, very particularly preferably from 20 to 60% by weight, of oxygen-containing compounds of copper, calculated as CuO, from 0 to 50% by weight, preferably from 0 to 30% by weight, particularly preferably from 0 to 20% by weight, of oxygen-containing compounds of magnesium, calculated as MgO, and/or oxygen-containing compounds of chromium, calculated as Cr$_2$O$_3$, and/or oxygen-containing compounds of zinc, calculated as ZnO, and/or oxygen-containing compounds of barium, calculated as BaO, and/or oxygen-containing compounds of calcium, calculated as CaO, and less than 20% by weight, preferably less than 10% by weight, particularly preferably less than 5% by weight, very particularly preferably less than 1% by weight, for example 0% by weight, of oxygen-containing compounds of nickel, calculated as NiO, based on the oxygen-containing compounds of copper, calculated as CuO.

The catalytic composition of preferred catalysts comprises from 20 to 85% by weight, preferably from 25 to 80% by weight, particularly preferably from 30 to 75% by weight, of aluminum oxide (Al$_2$O$_3$) and/or silicon dioxide (SiO$_2$) and no oxygen-containing compounds of zirconium and titanium.

The oxygen-containing compounds of copper are, in particular, copper(I) oxide and copper(II) oxide, preferably copper(II) oxide.

There are a number of possible methods for preparing the catalysts used in the process of the present invention. They can be obtained, for example, by peptization of pulverulent mixtures of the hydroxides, carbonates, oxides and/or other salts of the components aluminum, zirconium, titanium, silicon, copper, magnesium, chromium, zinc, barium and calcium with water and subsequent extrusion and heat treatment of the composition obtained in this way.

The catalysts used in the process of the present invention can also be produced by impregnation of zirconium dioxide (ZrO$_2$), titanium dioxide (TiO$_2$), aluminum oxide (Al$_2$O$_3$), silicon dioxide (SiO$_2$) or mixtures of two or more of these inorganic oxides which are, for example, in the form of powder or shaped bodies such as extrudates, pellets, spheres or rings.

Aluminum oxide can be used in various modifications, preference being given to α-, γ- or θ-Al$_2$O$_3$.

Zirkonium dioxide is used, for example, in the monoclinic or tetragonal form, preferably in the monoclinic form, and titanium dioxide is preferably used as anatase or rutile.

Silicon dioxide which is suitable as support material can be obtained, for example, by precipitation from water glass or by the sol-gel process or can be used in the form of mesoporous SiO$_2$ or silica gel (e.g. as described in Ullmann, Enzykl. Techn. Chem., 4th edition, volume 21, pp. 457–63, 1982) or in the form of silicates such as bentonite, montmorillonite, kaolin, hectorite or aluminosilicates (e.g. as described in Nature, volume 359, pp. 710–12, 1992 or alkali metal or alkaline earth metal aluminosilicates (zeolites), e.g. of the formula M$_{2/z}$O.Al$_2$O$_3$.xSiO$_2$.yH$_2$O, where M is a monovalent or polyvalent metal, H, [NH$_4$], z is the valence, x=1.8 to about 12 and y=0 to about 8, magnesium silicates (e.g. steatite), zirconium silicates, cerium silicates or calcium silicates.

Shaped bodies of the abovementioned inorganic oxides can be produced by customary methods.

The impregnation of these inorganic oxides is likewise carried out by customary methods, as described, for example, in EP-A-599 180, EP-A-673 918 or A. B. Stiles, Catalyst Manufacture-Laboratory and Commercial Preparations, Marcel Dekker, New York (1983), by application of an appropriate metal salt solution in one or more impregnation stages using, for example, appropriate nitrates, acetates or chlorides as metal salts. The composition is dried and, if desired, calcined after impregnation.

The impregnation can be carried out by the "incipient wetness" method in which the inorganic oxide or the mixture of inorganic oxides is moistened with an amount of impregnation solution corresponding to its water absorption capacity so that it is just saturated. However, the impregnation can also be carried out in excess solution.

In the case of multistage impregnation processes, it is advantageous to dry and, if appropriate, calcine the impregnated support between the individual impregnation steps. Multistage impregnation is advantageous particularly when the inorganic oxide or the mixture of inorganic oxides is to have a relatively large amount of metal applied to it.

To apply a plurality of metal components to the inorganic oxide or the mixture of inorganic oxides, the impregnation can be carried out using all metal salts simultaneously or using the individual metal salts in succession in any order.

However, precipitation methods are usually employed for preparing the catalysts used in the process of the invention. Thus, for example, they can be obtained by coprecipitation of the copper, magnesium, chromium, zinc, barium and calcium components from an aqueous salt solution comprising these elements by means of mineral bases in the presence of a slurry of a sparingly soluble, oxygen-containing aluminum, titanium, silicon and/or zirconium compound and subsequent washing, drying and calcination of the precipitate obtained. As sparingly soluble, oxygen-containing aluminum, titanium, silicon and/or zirconium compounds, it is possible to use, for example, aluminum oxide, titanium dioxide, silicon dioxide, zirconium dioxide and hydrated zirconium oxide. The slurries of the sparingly soluble aluminum, titanium, silicon and/or zirconium compounds can be prepared by suspending fine powders of these compounds in water with vigorous stirring. The slurries are advantageously obtained by precipitation of the sparingly soluble aluminum, titanium, silicon and/or zirconium compounds from aqueous aluminum, titanium, silicon and/or zirconium salt solutions by means of mineral bases.

The catalysts used in the process of the present invention are preferably prepared by coprecipitation of all their components. For this purpose, an aqueous salt solution comprising the catalyst components is advantageously treated hot and while stirring with an aqueous mineral base, in particular an alkali metal base, for example sodium carbonate, sodium hydroxide, potassium carbonate or potassium hydroxide, until precipitation is complete. The type of salts used is generally not critical: since this procedure is primarily dependent on the water-solubility of the salts, a criterion is that they have the good water-solubility required for producing these comparatively highly concentrated salt solutions. It is self-evident that when selecting the salts of the individual components, only salts having anions which do not lead to interference, whether by causing undesired precipitation or by hindering or preventing the precipitation as a result of complex formation, should be selected.

The precipitates obtained in these precipitation reactions are generally chemically uniform and comprise, inter alia, mixtures of the oxides, hydrated oxides, hydroxides, carbonates and insoluble and basic salts of the metals used. To improve the filterability of the precipitates, it may be found to be advantageous for them to be aged, i.e. for them to be left standing for some time after the precipitation, if desired hot or while passing air through.

The precipitates obtained by these precipitation processes are processed further to form the catalysts of the present invention in a customary manner. After washing, they are generally dried at from 80 to 200° C., preferably from 100 to 150° C., and then calcined. The calcination is generally carried out at from 300 to 800° C., preferably from 400 to 600° C., in particular from 450 to 550° C.

After calcination, the catalyst is advantageously conditioned, either by bringing it to a particular particle size by milling or by, after milling, mixing it with shaping aids such as graphite or stearic acid, pressing it by means of a press to form compounds, e.g. pellets, and heat-treating it. The heat treatment temperatures in this case generally correspond to the temperatures in the calcination.

In the catalysts produced in this way, the catalytically active metals are present in the form of a mixture of their oxygen-containing compounds, i.e. in particular as oxides and mixed oxides.

The catalysts produced in this way are stored and, if appropriate, treated as such. Before being used as catalysts for preparing bis(2-morpholinoethyl) ether from diethylene glycol and ammonia, they are usually prereduced. However, they can also be used without prereduction, in which case they are then reduced by the hydrogen present in the reactor under the conditions of the hydrogenative amination.

For the prereduction, the catalysts are generally first exposed to a nitrogen-hydrogen atmosphere at from 150 to 200° C. for from 12 to 20 hours and subsequently treated in a hydrogen atmosphere at from 200 to 400° C. for a further period of about 24 hours. During this prereduction, part of the oxygen-containing metal compounds present in the catalysts is reduced to the corresponding metals, so that these together with the various oxygen compounds are present in the active form of the catalyst.

The catalysts of the formula $M_xMg_y(SiO_2).nH_2O$, where M is a divalent, reducible metal atom selected from the group consisting of Cu, Fe, Co and Ni, x and y are numbers which together can reach a value of 1.5 and n after drying, expressed in % by weight, is from 0 to 80, disclosed in EP-A-284 919, for example the catalyst described in the example in loc. cit. and comprising 35% of CuO, 9% of MgO and 38% of $SiO_2$ and the catalyst described in page 3 of EP-A-863 140 and comprising from 45 to 47% by weight of CuO, magnesium silicate comprising from about 15 to 17% by weight of MgO and from 35 to 36% by weight of $SiO_2$, about 0.9% by weight of $Cr_2O_3$, about 1% by weight of BaO and about 0.6% by weight of ZnO, and the supported catalysts disclosed in WO 95/32171 and EP-A-816 350 and comprising from 5 to 50% by weight, preferably from 15 to 40% by weight, of copper, calculated as CuO, from 50 to 95% by weight, preferably from 60 to 85% by weight, of silicon, calculated as $SiO_2$ from 0 to 20% by weight of magnesium, calculated as MgO, 0 bis 5% by weight of barium, calculated as BaO, from 0 to 5% by weight of zinc, calculated as ZnO, and from 0 to 5% by weight of chromium, calculated as $Cr_2O_3$, in each case based on the total weight of the calcined catalyst, for example the catalyst disclosed on page 5 of EP-A-816 350 and comprising 30% by weight of CuO and 70% by weight of $SiO_2$, can be advantageously used in the process of the present invention.

In the process of the present invention, particular preference is given to using the catalysts disclosed in DE-A-24 45 303 which are obtainable by heat treatment of a basic copper- and aluminum-containing carbonate of the composition $Cu_mAl_6(CO_3)_{0.5}m\ O_3(OH)_{m+12}$, where m is any, not necessarily integral, number in the range from 2 to 6, at from 350 to 700° C., for example the copper-containing precipitated catalyst disclosed in loc. cit., Example 1, which is prepared by treating a solution of copper nitrate and aluminum nitrate with sodium bicarbonate and subsequently washing, drying and heat-treating the precipitate.

The process of the present invention can be carried out batchwise or preferably continuously as follows, with the catalyst preferably being installed as a fixed bed in the reactor.

The amination of the diethylene glycol can be carried out in the liquid phase or in the gas phase. Preference is given to a fixed-bed process in the gas phase.

Ammonia is generally used in a molar ratio of ammonia to diethylene glycol of from 1:1 to 50:1, preferably from 1.5:1 to 30:1, particularly preferably from 2:1 to 20:1, very particularly preferably from 2:1 to 6:1. The ammonia excess can also be greater than 50:1.

The hydrogen is generally fed into the reaction in an amount of from 5 to 400 l, preferably from 50 to 200 l, per mole of alcohol component, with the liter figures in each case being at STP.

When the reaction is carried out in the liquid phase, the starting materials diethylene glycol and ammonia are passed in the liquid phase together with hydrogen at from 100 to 300° C., preferably from 150 to 250° C., particularly preferably from 170 to 230° C., and pressures of from 0.1 to 30 MPa, preferably from 10 to 25 MPa, particularly preferably from 15 to 20 MPa, over the catalyst which is usually located in a fixed-bed reactor which is preferably heated externally (e.g. a tube reactor). Operation either in the downflow mode or in the upflow mode is possible. The space velocity over the catalyst is generally in the range from 0.05 to 1.0 kg of DEG per liter of catalyst (bed volume) and hour. If desired, the starting materials can be diluted with a suitable solvent, e.g. N-methylpyrrolidone. It is advantageous to preheat the reactants before introduction into the reaction vessel, preferably to the reaction temperature.

When the reaction is carried out in the gas phase, diethylene glycol in a gas stream comprising hydrogen and ammonia, preferably consisting of hydrogen and ammonia, which is sufficient for vaporization is passed over the catalyst at from 100 to 300° C., preferably from 150 to 250° C., particularly preferably from 170 to 230° C., and pressures of from 0.1 to 10 MPa, preferably from 1 to 5 MPa, particularly preferably from 1 to 3 MPa. It is possible for the stream to flow into the fixed catalyst bed either from above or from below. The gas stream required is preferably obtained by means of a circulating gas procedure. In such a procedure, for example, a circulating gas flow of from about 9 to 13 m$^3$/h (volume at STP) and an off-gas flow of from about 250 to 350 l/h is employed at a catalyst bed volume of 1.5 l. The space velocity over the catalyst is generally in the range from 0.1 to 0.8, preferably from 0.2 to 0.4, kg of DEG per liter of catalyst (bed volume) and hour.

Both when working in the liquid phase and when working in the gas phase, it is possible to employ higher temperatures, higher total pressures and higher space velocities over the catalyst. The pressure in the reaction vessel, which is given by the sum of the partial pressures of the aminating agent, the alcohol component and the reaction products formed and also any solvent used at the temperatures indicated, is advantageously increased to the desired reaction pressure by injection of hydrogen.

Both in a continuous reaction in the liquid phase and in a continuous reaction in the gas phase, the excess ammonia can be circulated together with the hydrogen.

The water of reaction formed during the reaction generally does not have an adverse effect on the degree of conversion, the reaction rate, the selectivity and the operating life of the catalyst and is therefore advantageously removed from the reaction product only when the latter is worked up, e.g. by distillation.

After the output from the reactor has advantageously been depressurized, the excess ammonia and the hydrogen are removed from it and the resulting crude reaction product which comprises essentially bis(2-morpholinoethyl) ether, morpholine, water and possibly unreacted diethylene glycol is fractionated by fractional rectification. For example, water and morpholine are first distilled off under atmospheric pressure, further morpholine and DEG are then distilled off at from about 5 to 20 mbar and pure DMDEE is finally isolated by rectification of the remaining crude product at from about 2 to 8 mbar.

The morpholine obtained as by-product and any unreacted diethylene glycol can be returned to the DMDEE synthesis.

EXAMPLE

Diethylene glycol together with ammonia and hydrogen was fed via a preheater into a tube reactor which had been charged with 1.5 l (bed volume) of a precipitated catalyst composed of 55% by weight of CuO and 45% by weight of gamma-Al$_2$O$_3$ (after its last heat treatment and before reduction with hydrogen) and was operated at a gauge pressure of 1.5 MPa (15 bar).

The catalyst was prepared by a method analogous to Example 1 of DE-A-24 45 303 and was reduced in a stream of hydrogen at about 200° C. before commencement of the reaction.

The reactor was at a temperature of from 215 to 225° C. and the circulating gas flow was about 11 standard m$^3$/h [standard m$^3$ =cubic meters at STP]. The process was operated at a small off-gas flow of about 300 standard l/h [standard l=liters at STP].

The molar ratio of diethylene glycol to ammonia was 1:3.6 and the space velocity of the catalyst was 0.4 kg of diethylene glycol and 0.23 kg of ammonia per 1.5 liters of catalyst (bed volume) and hour.

The output from the reactor was depressurized in a separator and analyzed by gas chromatography. The composition was as follows (in GC-% by area, ammonia- and water-free):

| | |
|---|---|
| morpholine: | 36.9 |
| N-ethylmorpholine: | 0.8 |
| monoaminodiglycol: | 1.4 |
| diethylene glycol: | 16.2 |
| bis (2-morpholinoethyl) ether: | 40.2 |
| others: | 4.5 |

This corresponded to a diethylene glycol conversion of 83.8%, a bis(2-morpholinoethyl) ether selectivity of 48% and thus a DMDEE yield of 40%.

The output from the reactor was subsequently worked up by distillation. Here, first water and N-ethylmorpholine and then morpholine were distilled off at atmospheric pressure in a 1 m column. Subsequently, further morpholine and then a mixture of monoaminodiglycol and DEG were distilled off at about 10 hPa (10 mbar). The DMDEE remained in the residue and was finally distilled via a 30 cm column at about 5 mbar and a bottom temperature of 190° C. After a small amount of first runnings, the DMDEE was obtained in a purity of greater than 99.5% (according to GC). Excess ammonia and unreacted diethylene glycol were returned to the reaction after the work-up by distillation.

We claim:

1. A process for preparing bis(2-morpholinoethyl) ether by reacting diethylene glycol with ammonia under superatmospheric pressure and at elevated temperature in the presence of hydrogen and a hydrogenation catalyst, wherein the catalytically active composition of the catalyst prior to reduction with hydrogen comprises from 20 to 85% by weight of aluminum oxide (Al$_2$O$_3$), zirconium dioxide (ZrO$_2$), titanium dioxide (TiO$_2$) and/or silicon dioxide (SiO$_2$), from 1 to 70% by weight of oxygen-containing compounds of copper, calculated as CuO, from 0 to 50% by weight of oxygen-containing compounds of magnesium, calculated as MgO, oxygen-containing compounds of chromium, calculated as Cr$_2$O$_3$, oxygen-containing compounds of zinc, calculated as ZnO, oxygen-containing compounds of barium, calculated as BaO, and/or oxygen-containing compounds of calcium, calculated as CaO, and less than 20% by weight of oxygen-containing compounds of nickel, calculated as NiO, based on the oxygen-containing compounds of copper, calculated as CuO.

2. A process as claimed in claim 1, wherein the catalytically active composition of the catalyst prior to reduction with hydrogen comprises less than 10% by weight of oxygen-containing compounds of nickel, calculated as NiO, based on the oxygen-containing compounds of copper, calculated as CuO.

3. A process as claimed in claim 1, wherein the catalytically active composition of the catalyst prior to reduction with hydrogen comprises less than 5% by weight of oxygen-containing compounds of nickel, calculated as NiO, based on the oxygen-containing compounds of copper, calculated as CuO.

4. A process as claimed in claim 1, wherein the catalytically active composition of the catalyst prior to reduction with hydrogen comprises from 30 to 75% by weight of aluminum oxide ($Al_2O_3$), zirconium dioxide ($ZrO_2$), titanium dioxide ($TiO_2$) and/or silicon dioxide ($SiO_2$), from 5 to 60% by weight of oxygen-containing compounds of copper, calculated as CuO, and from 0 to 20% by weight of oxygen-containing compounds of magnesium, calculated as MgO, oxygen-containing compounds of chromium, calculated as $Cr_2O_3$, oxygen-containing compounds of zinc, calculated as ZnO, oxygen-containing compounds of barium, calculated as BaO, and/or oxygen-containing compounds of calcium, calculated as CaO.

5. A process as claimed in claim 1, wherein the reaction is carried out in the gas phase.

6. A process as claimed in claim 1, wherein the reaction is carried out at from 100 to 300° C.

7. A process as claimed in claim 1, wherein the reaction is carried out at a pressure of from 0.1 to 30 MPa.

8. A process as claimed in claim 1, wherein the molar ratio of ammonia to diethylene glycol is from 1:1 to 50:1.

* * * * *

REEXAMINATION CERTIFICATE (4548th)
United States Patent
Riechers et al.

(10) Number: US 6,111,100 C1
(45) Certificate Issued: Apr. 2, 2002

(54) PREPARATION OF BIS(2-MORPHOLINOETHYL) ETHER

(75) Inventors: Hartmut Riechers, Neustadt; Joachim Simon, Mannheim; Andreas Henne, Neustadt; Arthur Höhn, Kirchheim, all of (DE)

(73) Assignee: BASF Aktiengesellschaft, Ludwigshafen (DE)

Reexamination Request:
No. 90/005,898, Dec. 28, 2000

Reexamination Certificate for:
Patent No.: 6,111,100
Issued: Aug. 29, 2000
Appl. No.: 09/474,906
Filed: Dec. 30, 1999

(30) Foreign Application Priority Data

Jan. 14, 1999 (DE) .......................................... 199 01 198

(51) Int. Cl.⁷ ............................................ C07D 413/12
(52) U.S. Cl. ....................................................... 544/87
(58) Field of Search ........................................... 544/87

(56) References Cited

U.S. PATENT DOCUMENTS 3,155,657 A   11/1964   Bedoit ........................ 260/247
4,739,051 A   4/1988   Schroeder et al. .......... 544/106

*Primary Examiner*—Richard L. Raymond

(57) ABSTRACT

In a process for preparing bis(2-morpholinoethyl) ether by reacting diethylene glycol with ammonia under superatmospheric pressure and at elevated temperature in the presence of hydrogen and a hydrogenation catalyst, the catalytically active composition of the catalyst prior to reduction with hydrogen comprises from 20 to 85% by weight of aluminum oxide ($Al_2O_3$), zirconium dioxide ($ZrO_2$), titanium dioxide ($TiO_2$) and/or silicon dioxide ($SiO_2$), from 1 to 70% by weight of oxygen-containing compounds of copper, calculated as CuO, from 0 to 50% by weight of oxygen-containing compounds of magnesium, calculated as MgO, oxygen-containing compounds of chromium, calculated as $Cr_2O_3$, oxygen-containing compounds of zinc, calculated as ZnO, oxygen-containing compounds of barium, calculated as BaO, and/or oxygen-containing compounds of calcium, calculated as CaO, and less than 20% by weight of oxygen-containing compounds of nickel, calculated as NiO, based on the oxygen-containing compounds of copper, calculated as CuO.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

* * * * *